United States Patent
Voloshin et al.

(10) Patent No.: US 6,988,988 B2
(45) Date of Patent: *Jan. 24, 2006

(54) ENDOSCOPIC INSPECTION USING A FLEXIBLE SLEEVE

(75) Inventors: Michael Voloshin, Haifa (IL); Yackov Bar-Or, Haifa (IL); Victor Levin, Haifa (IL); Giora Bernat, Haifa (IL); Dan Oz, Even-Yehuda (IL)

(73) Assignee: Sightline Technologies Ltd., Haifa (IL)

( * ) Notice: Subject to any disclaimer, the term of this patent is extended or adjusted under 35 U.S.C. 154(b) by 133 days.

This patent is subject to a terminal disclaimer.

(21) Appl. No.: 10/267,193

(22) Filed: Oct. 9, 2002

(65) Prior Publication Data

US 2003/0105386 A1   Jun. 5, 2003

Related U.S. Application Data

(63) Continuation of application No. 09/646,941, filed on Nov. 13, 2000, now Pat. No. 6,485,409.

(30) Foreign Application Priority Data

Jan. 29, 1999   (IL) ..................................... 128286

(51) Int. Cl.
  *A61B 1/00*  (2006.01)
  *A61B 1/31*  (2006.01)

(52) U.S. Cl. ...................... 600/115; 600/101; 600/152

(58) Field of Classification Search ................ 600/101, 600/114, 115, 152, 116; 604/95.01, 95.03, 604/271

See application file for complete search history.

(56) References Cited

U.S. PATENT DOCUMENTS

| 3,279,460 A | 10/1966 | Sheldon |
| 3,895,637 A | 7/1975 | Choy |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,207,872 A | 6/1980 | Meiri et al. |
| 4,321,915 A | 3/1982 | Leighton et al. |
| 4,403,985 A | 9/1983 | Boretos |
| 4,444,462 A | 4/1984 | Ono et al. |
| 4,655,673 A | 4/1987 | Hawkes |
| 4,723,912 A * | 2/1988 | Nieusma ..................... 433/116 |

(Continued)

FOREIGN PATENT DOCUMENTS

EP   0 338 557 A1   10/1989

(Continued)

OTHER PUBLICATIONS

Translation of Inventors Certificate SU 1522466.*

*Primary Examiner*—John P. Leubecker
(74) *Attorney, Agent, or Firm*—Darby & Darby

(57) ABSTRACT

An endoscopic apparatus including an internal unit, adapted to be advanced into a gastrointestinal tract of a patient so as to enable inspection of the tract, an anchor unit, adapted to be held in a position outside the gastrointestinal tract and a flexible sleeve, having a proximal end fixed to the anchor and a distal end fixed to the internal unit, wherein at least a portion of the sleeve between the proximal end distal ends is held initially in a compact state at the internal unit and is arranged to feed out from the internal unit as the internal unit is advanced into the gastrointestinal tract. A method for endoscopic examination is also disclosed.

3 Claims, 3 Drawing Sheets

U.S. PATENT DOCUMENTS

| | | | |
|---|---|---|---|
| 4,735,501 A | 4/1988 | Ginsburgh et al. | |
| 4,868,644 A | 9/1989 | Yabe et al. | |
| 4,884,133 A | 11/1989 | Kanna et al. | |
| 5,045,070 A | 9/1991 | Grodecki et al. | |
| 5,051,824 A | 9/1991 | Nishigaki | |
| 5,125,143 A | 6/1992 | Takahashi | 29/237 |
| 5,203,319 A | 4/1993 | Danna et al. | |
| 5,259,364 A | 11/1993 | Bob et al. | |
| 5,372,124 A | 12/1994 | Takayama et al. | |
| 5,398,670 A * | 3/1995 | Ortiz et al. | 385/119 |
| 5,483,951 A | 1/1996 | Frassica et al. | 600/104 |
| 5,496,259 A | 3/1996 | Perkins | |
| 5,586,968 A | 12/1996 | Grundl et al. | |
| 5,604,531 A | 2/1997 | Iddan et al. | |
| 5,626,607 A | 5/1997 | Malacki et al. | |
| 5,656,117 A * | 8/1997 | Wood et al. | 156/287 |
| 5,662,587 A * | 9/1997 | Grundfest et al. | 600/114 |
| 5,681,260 A | 10/1997 | Ueda et al. | |
| 5,704,899 A | 1/1998 | Milo | 600/161 |
| 5,817,015 A | 10/1998 | Adair | 600/121 |
| 5,827,177 A | 10/1998 | Oneda et al. | 600/121 |
| 6,123,080 A * | 9/2000 | Mohan et al. | 128/849 |
| 6,224,543 B1 | 5/2001 | Gammons et al. | |
| 6,241,740 B1 | 6/2001 | Davis et al. | |
| 6,293,907 B1 | 9/2001 | Axon et al. | |
| 6,416,462 B1 | 7/2002 | Tovey et al. | |
| 6,702,735 B2 | 3/2004 | Kelly | |

FOREIGN PATENT DOCUMENTS

| | | | |
|---|---|---|---|
| EP | 0 745 347 B1 | | 5/1996 |
| GB | 2 231 231 | | 11/1990 |
| GB | 2306111 A | * | 4/1997 |
| SU | 1 522 466 A1 | | 8/1978 |
| WO | WO 86/06944 | | 5/1986 |
| WO | WO 97/32515 | | 3/1997 |
| WO | WO-99/17655 A1 | | 4/1999 |
| WO | WO-00/44275 A1 | | 8/2000 |

* cited by examiner

ENDOSCOPIC INSPECTION USING A FLEXIBLE SLEEVE

This application is a continuation of U.S. patent application Ser. No. 09/646,941, filed Nov. 13, 2000, now U.S. Pat. No. 6,485,409.

FIELD OF THE INVENTION

The present invention relates generally to propulsion of objects within lumens, and specifically to methods and devices for propelling medical instruments through the colon

BACKGROUND OF THE INVENTION

The use of an endoscope for examining a body cavity is well known in the art The diagnostic and therapeutic advantages conferred by direct examination of the gastrointestinal tract with a flexible endoscope have made this method a standard procedure of modern medicine. One of the most common endoscopic procedures is colonoscopy, which is performed for a wide variety of purposes, including diagnosis of cancer, determination of the source of gastrointestinal bleeding, viewing a site affected by inflammatory bowel disease, removing polyps, and reducing volvulus and intussusception.

While colonoscopy is useful and effective, it is a difficult procedure for a physician to perform and is painful and occasionally dangerous for the patient These problems stem from the need to push and steer the long, flexible colonoscope through the intestine by pushing it in from its proximal end, outside the body.

It would be desirable to provide a propulsion mechanism to push or pull the endoscope forward from its distal end, inside the body. A number of methods and devices have been proposed for this purpose, although none has achieved clinical or commercial acceptance.

U.S. Pat. No. 4,207,872 to Meiri et al., whose disclosure is incorporated herein by reference, describes a device and method for advancing an endoscope through a body passage utilizing multiple fluid-filled flexible protrusions distributed along an outer surface of a sleeve containing the endoscope. Alternately increasing and decreasing the fluid pressure within the protrusions advances the endoscope along a body passage. Each protrusion is in direct contact with an inner surface of the body passage and applies local contact pressure against this relatively small contact surface in order to propel the endoscope forward.

U.S. Pat. No. 3,895,637 to Choy, whose disclosure is incorporated herein by reference, describes a device able to move through a tubular organ by sequentially inflating and deflating first and second radially inflatable members The inflation anchors the inflated member against a local region of the tubular organ, while air pressure in a longitudinally inflatable communicating part of the device moves the non-anchored part of the device longitudinally through the tubular organ Sufficient contact pressure of the inflated member against a relatively small length of the tubular organ is required in order for the device to be able to progress through the organ U.S. Pat. No. 3,895,637 has no provision to distribute the contact pressure over a larger area of the tissue against which it presses in order to generate longitudinal motion.

U.S. Pat. No. 4,321,915 to Leighton et al, whose disclosure is incorporated herein by reference, describes an everting tube device for introducing a tool into a body cavity using alternating steps of applying positive pressure to evert the tube and advance the tool, and applying a vacuum to pull the everted tube away from the tool so that an operator can retract the tool one half of the distance it advanced in the previous step The operator using this device is required to manually withdraw the tool the prescribed distance during every pressure cycle in order to avoid causing the tool to advance too far beyond the tip of the everted tube U.S. Pat. No. 4,403,985 to Boretos, whose disclosure is incorporated herein by reference, describes a jet-propelled device for insertion into body passageways Pressurized fluid is passed to the device from outside of the body and then ejected from an orifice in the device in one direction in order to propel the device in the opposite direction. The device of U.S. Pat. No. 4,403,985 thus generates propulsion by expelling material into the body passageway

SUMMARY OF THE INVENTION

It is an object of some aspects of the present invention to provide an improved system and method for propelling an object within a lumen.

It is a further object of some aspects of the present invention to provide an improved propulsion mechanism for advancing an endoscope within a body cavity of a patient for purposes of examination, diagnosis, and treatment.

In preferred embodiments of the present invention, a probe containing an endoscopic instrument is advanced through the lower gastrointestinal tract of a patient by inflation of a flexible sleeve coupled to the probe. One end of the sleeve is anchored, typically at or adjacent to the patient's anus. As the sleeve is inflated, preferably using a pressurized gas, the probe is propelled forward, and the sleeve is fed out gradually between the probe and the anus. The portion of the sleeve that is inflated expands radially outward and remains substantially stationary relative to the intestinal wall as long as it is inflated Longitudinal motion of the sleeve relative to the wall generally occurs only at and adjacent to the probe itself The probe is thus advanced easily, and trauma to the gastrointestinal tract is minimized. To remove the probe, the sleeve is deflated and is used to pull the probe back out through the anus.

In some preferred embodiments of the present invention, the sleeve is passed around the probe and everts as the probe advances. Preferably, the sleeve is folded over one or more resilient rings encircling the probe, wherein the rings most preferably comprise ring-shaped springs, which encircle the outer surface of the probe and are held against the probe by magnetic attraction. Inflating the sleeve advances the probe through the colon, causing the sleeve to unfold from the inside out. Thus, an external portion of the sleeve opens out only near the probe, while the rest of the external portion stays stationary.

In other preferred embodiments of the present invention, the sleeve is stored in a compact state, typically folded or rolled up, inside or immediately adjacent to the probe. Most preferably, the folded or rolled-up probe is stored in a recess in a proximal portion of the probe. As the probe advances, the sleeve feeds gradually out of its stored state and expands against the intestinal wall.

In some preferred embodiments of the present invention, the probe comprises a separate steering unit for easing over or around curves in the gastrointestinal tract and obstructions, such as blood clots, small deformations and other obstacles, so that the probe can move within the patient's body while minimizing harmful contact and friction The steering unit preferably works by gas or fluid pressure, most preferably as described in Israel Patent Application 125,397, which is assigned to the assignee of the present patent application and whose disclosure is incorporated herein by reference. Alternatively, other steering methods known in the art may be used.

In some preferred embodiments of the present invention, the probe comprises instruments for examination, diagnosis and treatment Preferably, the instruments include an imaging device, most preferably a miniature video camera and light source, as are known in the art, which are used to capture endoscopic images. Means for operating the instruments and receiving data therefrom comprise wires, fiber-optic lines, or tubes which are coupled to the instruments and extend to an operator or to equipment outside of the patient, which operates the instruments and receives data therefrom. The wires, line or tubes preferably pass through the sleeve.

In preferred embodiments of the present invention, advancing the probe through the gastrointestinal tract by way of inflating the sleeve reduces or eliminates the necessity of applying mechanical force at a proximal end of the probe (outside the patient's body) to insert the probe, as is required using conventional endoscopes The present invention thus reduces or eliminates the necessity of applying concentrated, local pressure to any part the patient's body, reduces or eliminates rubbing and friction between the unit or parts of it and the patient's body, and avoids ejecting fluids or other materials into the body's passageway.

There is therefore provided, in accordance with a preferred embodiment of the present invention, endoscopic apparatus which advances within a lumen, including:

a probe having distal and proximal ends; and a flexible sleeve coupled proximally to the probe, which sleeve is inflated in order to propel the probe within the lumen Preferably, the probe includes an imaging device, which captures images inside the lumen.

In a preferred embodiment, the sleeve everts as the probe advances, wherein the sleeve is passes around an outer surface of the probe and everts over a retaining ring, which holds the sleeve against the outer surface of the probe Preferably, the probe includes magnetic material, and wherein the retaining ring includes one or more metal springs, which are held against the probe by magnetic attraction thereto Further preferably, an outer portion of the sleeve, which has everted over the ring, is anchored so as to remain substantially stationary relative to a wall of the lumen.

In another preferred embodiment, a portion of the sleeve is held at the probe in a compact state and feeds out from the proximal end of the probe as the probe advances. Preferably, the probe has a recess adjacent to the proximal end thereof, which contains the sleeve in the compact state Further preferably, the sleeve is anchored at a position proximal to the probe so that a portion of the sleeve that has been inflated, between the proximal position and the probe, remains substantially stationary relative to a wall of the lumen Preferably, the lumen includes a passage inside the body of a patient, most preferably a portion of the gastrointestinal tract There is also provided, in accordance with a preferred embodiment of the present invention, a method for propelling a probe within a lumen, including coupling a flexible sleeve to a proximal end of the probe; and inflating the sleeve to advance the probe through the lumen In a preferred embodiment, the sleeve everts as the probe is advanced, wherein coupling the sleeve includes passing the sleeve around an outer surface of the probe and folding the sleeve over a retaining ring, which holds the sleeve against the outer surface of the probe Preferably, the method includes anchoring an everted, outer portion of the sleeve so as to remain substantially stationary relative to a wall of the lumen.

In another preferred embodiment, coupling the sleeve includes holding a portion of the sleeve in a compact state at the proximal end of the probe, so that the sleeve feeds out from the proximal end as the probe advances.

Preferably, the lumen includes the gastrointestinal tract of a patient.

The present invention will be more fully understood from the following detailed description of the preferred embodiments thereof, taken together with the drawings, in which.

DETAILED DESCRIPTION OF A PREFERRED EMBODIMENTS

Figure 1:
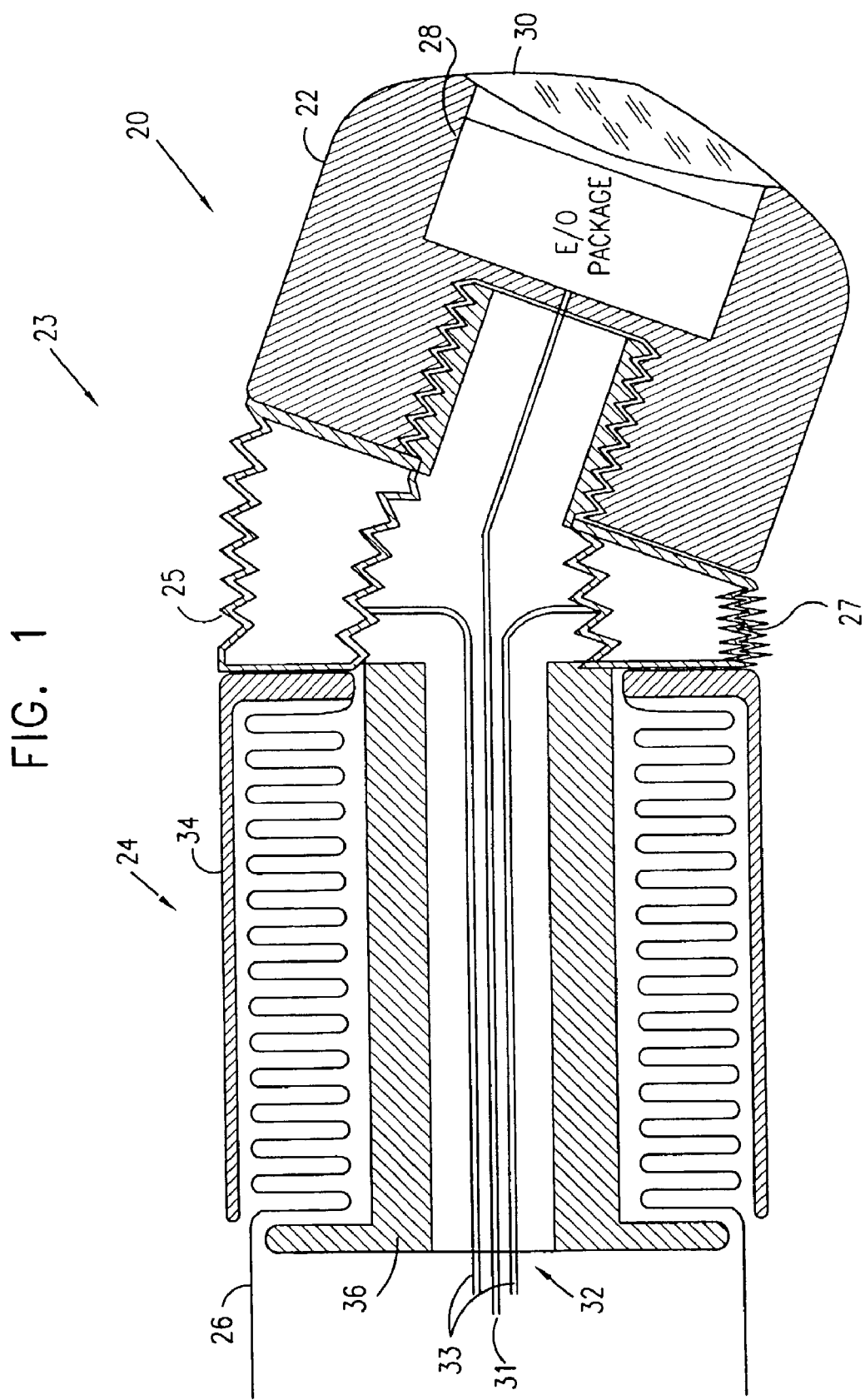
FIG. 1 is a schematic, sectional illustration of a probe with a folded sleeve, in accordance with a preferred embodiment of the present invention.

FIG. 1 is a schematic, sectional illustration of an endoscopic probe 20, in accordance with a preferred embodiment of the present invention. Probe 20 comprises a probe head or top 22, which is preferably cylindrically shaped with a transparent optical window or lens 30 at its distal end The probe contains an electro-optical package 28, which preferably includes a light source and miniature video camera, as are known in the art, which capture images through lens 30. A cable bundle 32 includes wires 31, which connect package 28 and an external console for use in transmitting information from and to the package.

The probe further comprises a base 24, made up of a cap 34, which receives an covers and an internal spindle 36, flanged at its proximal end. A flexible sleeve 26 is folded into the space between the cap and the spindle, and feeds out of a circular slot formed between the cap and the spindle at the proximal end of the base Cable 32 preferably passes through a hollow bore in the center of spindle 36, as shown in the figure.

Sleeve 26 preferably comprises a flexible, biocompatible plastic, of any suitable type known in the art, most preferably with a wall thickness between about 0 1 and 0.5 mm and an overall diameter when inflated of about 10 mm. The plastic sleeve 26 is folded and fastened tightly within base 24, so as to allow the sleeve to unfold and feed out evenly from the proximal to the distal end thereof The distal end of the sleeve is firmly sealed to probe 20, so the the sleeve can be inflated with pressurized gas or other fluid, as described further hereinbelow.

Preferably, probe 20 includes a steering unit 23, which angles probe head 22 relative to base 24 The steering unit is used to aid in turning the probe around curves and avoiding obstructions in the gastrointestinal tract. It is also useful in tilting head 22 so as to capture an image of or perform a surgical procedure on an area of interest that is not directly in front of the probe. Most preferably, steering unit 23 comprises a group of opposing bellows 25 and 27, as described in the above-mentioned Israel Patent Application 125,397, which are inflated and deflated by gas or fluid lines 33 within bundle 32 in order to turn the unit Although for simplicity, only two such bellows are shown in the figure, it will be understood that one, three, four or more bellows may actually be used Alternatively, steering unit 23 may comprise other types of steering mechanisms, as are known in the endoscopic art, such as mechanisms based on pull-wires In addition to electro-optic package 28, probe head 22 may also comprise suction and/or irrigation ports, sensors of various types and/or specially adapted surgical instruments, such as biopsy forceps. These elements are known generally in the art, and are not shown in the figures. Substantially any suitable type of tool or sensor may be adapted and included in head 22, and coupled to external apparatus by appropriate adaptation of cable 32.

Figure 2:
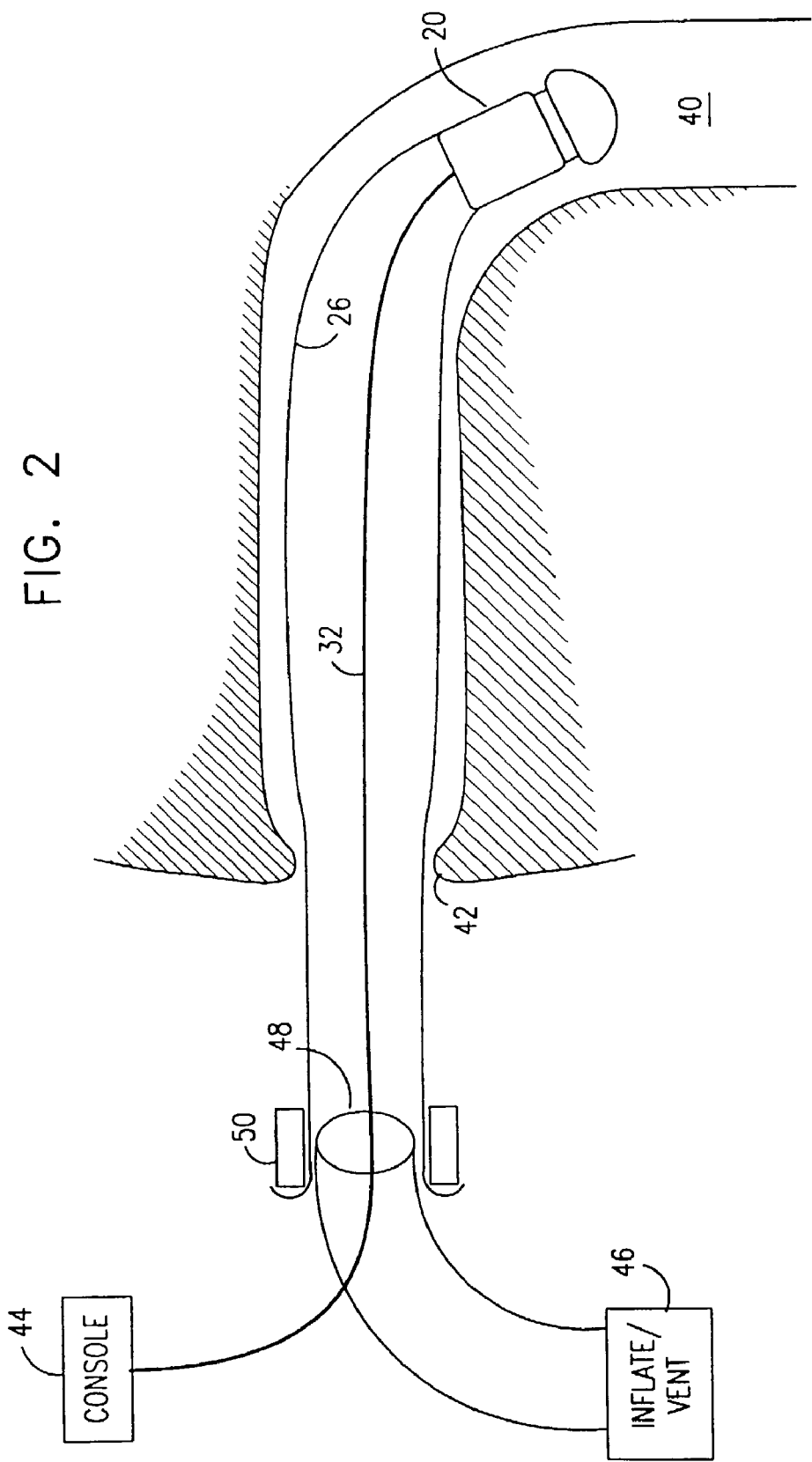
FIG. 2 is a schematic, partly sectional illustration, showing the probe of FIG. 1 and associated apparatus in operation, in accordance with a preferred embodiment of the present invention.

FIG. 2 is a schematic, partly sectional illustration of probe 20 in use for endoscopic examination of a patient's colon 40, in accordance with a preferred embodiment of the present invention A proximal end of sleeve 26 is fixed by a stationary anchor 50, located outside the patient's body, to a tube 48, which is coupled to inflation and venting apparatus 46. Cable 32 is fed through sleeve 26 and tube 48 via an air-tight coupling to a console 44.

Probe 20 is inserted into colon 40 through anus 42. Apparatus 46 is then actuated, for example, by opening a valve therein coupled to a regulated, pressurized source of $CO_2$ or other gas. Preferably, a gas pressure in the range of 0.3 atm is used to inflate the sleeve. Alternatively, a liquid, such as sterile water, may be used to inflate the sleeve. Inflating the sleeve propels probe 20 forward into colon 40, thus causing sleeve 26 to unfold and feed out of base 24 of the probe. The inflated portion of the sleeve typically expands radially and may contact the wall of the colon, but there is generally only minimal or no longitudinal motion of the sleeve against the wall Thus, rubbing and trauma to the intestinal wall are minimized.

As probe 20 passes through the colon, steering unit 23 is used as necessary, as described hereinabove, to turn probe head 22 at an angle relative to base 24. The steering unit is preferably controlled via console 44 to maneuver the probe around curves and obstructions in the gastrointestinal tract.

When the endoscopic examination is completed, apparatus 46 is operated to vent sleeve 26. The pressure in the sleeve is relieved, and the sleeve deflates. At this point probe 20 is withdrawn from colon 40, preferably by pulling on cable 32, or on deflated sleeve 26, or both.

Figure 3:
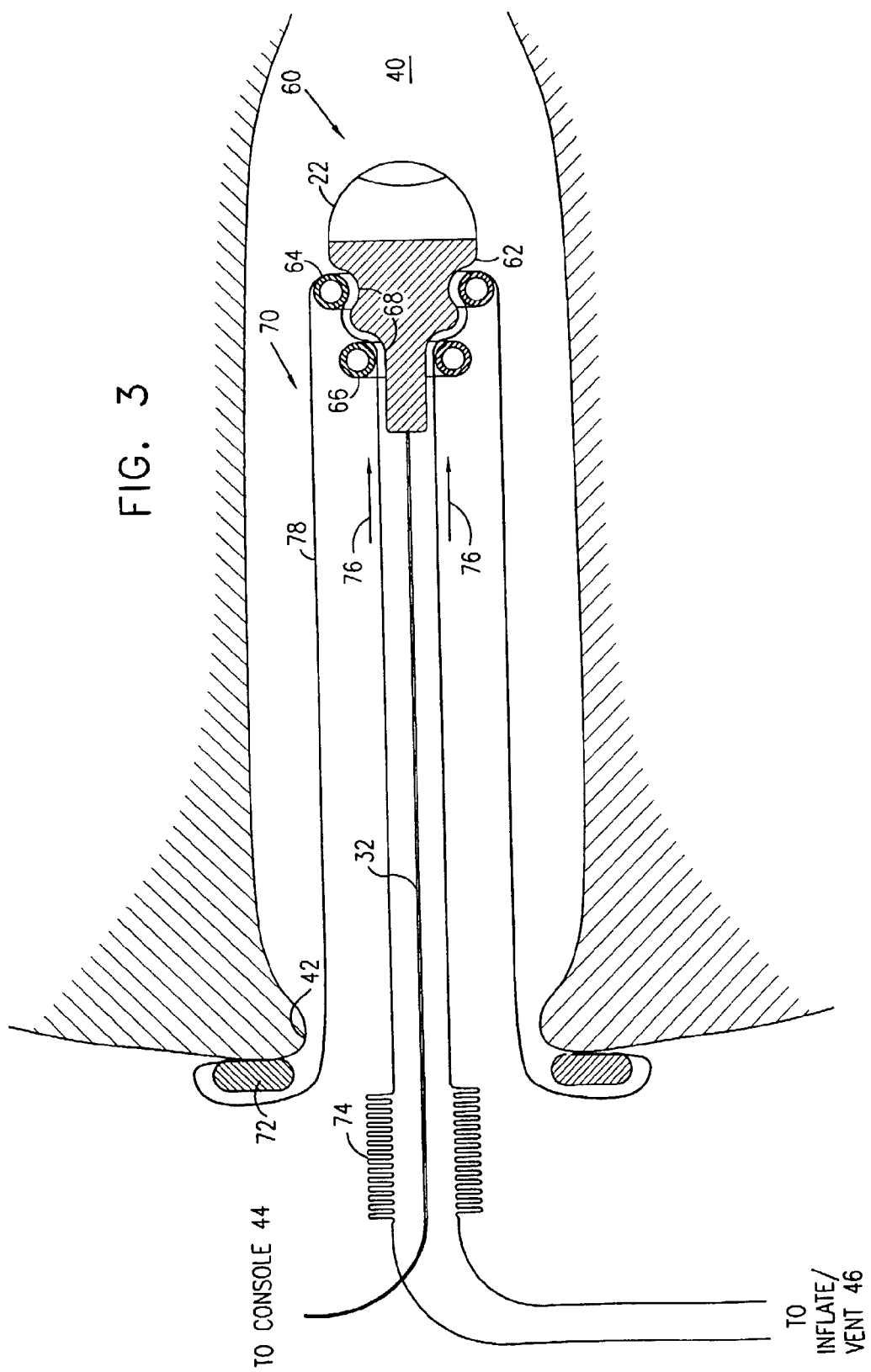
FIG. 3 is a schematic, sectional illustration of a probe with an everting sleeve, in accordance with another preferred embodiment of the present invention

FIG. 3 is a schematic, sectional illustration of another probe 60, with an everting sleeve 70, advancing inside colon 40, in accordance with a preferred embodiment of the present invention Probe 60 is generally similar in construction and operation to probe 20, described hereinabove, except for the operation of everting sleeve 70

A base 62 of probe 60 is preferably made of a magnetic metal and/or contains a permanent magnet Base 62 has two grooves 68, which receive respective magnetic metal springs 64 and 66, which have the form of resilient rings The circumference of groove 66 is preferably less than the circumference of groove 64, so that spring 64 is longer than spring 66 The resilience of springs 64 and 66 and their magnetic attraction to base 62 serves to retain sleeve 70 between the springs and the base.

Before inserting probe 60 through anus 42, sleeve 70 is passed around base 62, and springs 64 and 66 are fitted around the sleeve and into grooves 68. Sleeve 70 is then folded outward, or everted, over spring 64. An outer portion 78 of the sleeve is drawn through the springs and fastened to an anchor 72. A reserve portion 74 of sleeve 70 is folded or rolled up and held in a position outside the patient's body (as opposed to the case of probe 20, shown in FIG. 1, in which the reserve portion of the sleeve is held in the base of the probe)

To advance probe 60 in colon 40, sleeve 70 is inflated by inflation/venting apparatus 46. Reserve portion 74 unfolds, and an inner portion 76 thereof is pulled behind the probe in a distal direction, as shown by the arrows in FIG. 3, and everts over spring 64. Portion 76, which is moving, is contained inside outer portion 78, which contacts the wall of colon 40 and is substantially stationary. Thus, friction with or trauma to colon 40 are avoided. When it is time to withdraw probe 60, sleeve 70 is vented, and inner portion 76 is pulled back, away from the patient's body, thus reversing the everting action Preferably, springs 64 and 66 press sufficiently tightly against sleeve 70 in grooves 68, and the sleeve itself is sufficiently elastic, so as to produce a substantially air-tight seal. Thus, the gas that passes through reserve portion 74 to inflate the sleeve does not leak out in large quantities into colon 40. Alternatively, the space between inner portion 76 and outer portion 78 is inflated to advance probe 60

Although preferred embodiments are described hereinabove with reference to a device for moving an instrument package through the lower gastrointestinal tract, it will be understood that the novel principles of the present invention may be used to move objects in other body cavities, and may also be used to move objects in lumens and other regions for non-medical applications, as well An example of a non-medical application includes examination within a highly corrosive or high-temperature environment, where it is not desirable to have moving parts of a propulsion unit exposed to the environment It is also understood that while the preferred embodiments described hereinabove have physical data leads and control leads, the propulsion unit and instrument package can be powered by batteries and can store data and/or transmit data by wireless communications, as is known in the art.

It will thus be appreciated that the preferred embodiments are cited herein by way of example, and the full scope of the invention is limited only by the claims.

What is claimed is:

1. A method for endoscopic examination, comprising:
   coupling a proximal end of a flexible sleeve to an anchor unit;
   coupling a distal end of the sleeve to an internal unit, while gathering at least a portion of the sleeve between the proximal and distal ends in a compact state in the internal unit; and
   advancing the internal unit into a gastrointestinal tract of a patient while holding the anchor unit outside the gastrointestinal tract, so that the sleeve feeds out from the internal unit as the internal unit advances such that a proximal part of the portion of the sleeve is extended within the gastrointestinal tract while a distal part of the portion of the sleeve remains in the compact state in the internal unit;

inspecting the gastrointestinal tract using the internal unit; and deflating the sleeve in order to withdraw the internal unit from the gastrointestinal tract.

2. A method according to claim 1, wherein holding the anchor unit comprises anchoring the proximal end of the sleeve so that the sleeve that has fed out from the internal unit remains substantially stationary relative to a wall of the gastrointestinal tract as the internal unit is advanced.

3. The method of claim 1 wherein advancing the internal unit comprises inflating the sleeve.

* * * * *